United States Patent
Hammer et al.

(10) Patent No.: US 7,538,262 B2
(45) Date of Patent: May 26, 2009

(54) GDC-2 GENES CONFERRING HERBICIDE RESISTANCE

(75) Inventors: Philip E. Hammer, Cary, NC (US); Todd K. Hinson, Rougemont, NC (US); Nicholas B. Duck, Apex, NC (US)

(73) Assignee: Athenix Corporation, Research Triangle Park, NC (US)

( * ) Notice: Subject to any disclaimer, the term of this patent is extended or adjusted under 35 U.S.C. 154(b) by 333 days.

(21) Appl. No.: 11/185,560

(22) Filed: Jul. 20, 2005

(65) Prior Publication Data

US 2006/0021094 A1 Jan. 26, 2006

Related U.S. Application Data

(63) Continuation-in-part of application No. 10/797,416, filed on Mar. 10, 2004, now abandoned.

(60) Provisional application No. 60/453,149, filed on Mar. 10, 2003.

(51) Int. Cl.
   - A01H 5/10 (2006.01)
   - C12N 15/82 (2006.01)
   - C12N 15/52 (2006.01)
   - C12N 15/63 (2006.01)

(52) U.S. Cl. .................. 800/300; 435/410; 435/320.1; 435/252.3; 536/23.2; 800/288; 800/298

(58) Field of Classification Search .................. None
See application file for complete search history.

(56) References Cited

U.S. PATENT DOCUMENTS

| | | |
|---|---|---|
| 4,535,060 A | 8/1985 | Comai |
| 4,769,061 A | 9/1988 | Comai |
| 5,094,945 A | 3/1992 | Comai |
| 5,188,642 A | 2/1993 | Shah et al. |
| 5,463,175 A | 10/1995 | Barry et al. |
| 5,605,011 A | 2/1997 | Bedbrook et al. |
| 6,448,476 B1 | 9/2002 | Barry |

FOREIGN PATENT DOCUMENTS

| | | |
|---|---|---|
| WO | WO 02/36782 A2 | 5/2002 |
| WO | WO 02/36787 A2 | 5/2002 |

OTHER PUBLICATIONS

Kishore, G.M., and Jacob, G.S., "Degradation of Glyphosate by *Pseudomonas* sp. PG2982 via a Sarcosine Intermediate," *J. Biol. Chem.*, Sep. 5, 1987, pp. 12164-12168, vol. 262, No. 25.
Saari, L.L., et al., "Resistance to Acetolactate Synthase Inhibiting Herbicides," *Herbicide Resistance in Plants*, 1994, pp. 83-139, CRC Press, Inc.
Shinabarger, D.L. and Braymer, H.D., "Glyphosate Catabolism by *Pseudomonas* sp. Strain PG2982," *J. Bacteriol.*, Nov. 1986, pp. 702-707, vol. 168, No. 2.
Stock, M., et al., "Degradation of Glyphosate in Excised Leaves of Tobacco and Sugar Beet," *J. Plant Physiol.*, 1991, pp. 171-174, vol. 139, No. 2.
Wackett, L.P., et al., "Bacterial Carbon-Phosphorus Lyase: Products, Rates, and Regulation of Phosphonic and Phosphinic Acid Metabolism," *J. Bacteriol.*, Feb. 1987, pp. 710-717, vol. 169, No. 2.
NCBI Database Report for Accession No. AF013601, Direct Submission on Jul. 11, 1997.
NCBI Database Report for Accession No. AF098293, Direct Submission on Oct. 13, 1998.
UniProt Database Report for Accession No. 013331, Jan. 1, 1998, updated Mar. 1, 2004 (XP-002316626).

*Primary Examiner*—David H Kruse
(74) *Attorney, Agent, or Firm*—Alston & Bird LLP

(57) ABSTRACT

Compositions and methods for conferring herbicide resistance to plants, plant cells, tissues and seeds are provided. Compositions comprising a coding sequence for a polypeptide that confers resistance or tolerance to glyphosate herbicides are provided. The coding sequences can be used in DNA constructs or expression cassettes for transformation and expression in plants. Compositions also comprise transformed plants, plant cells, tissues, and seeds. In particular, isolated nucleic acid molecules corresponding to glyphosate resistant nucleic acid sequences are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:3 or the nucleotide sequences set forth in SEQ ID NOS:1 and 2.

17 Claims, 1 Drawing Sheet

SEQUENCE LISTING

```
<160> NUMBER OF SEQ ID NOS: 6

<210> SEQ ID NO 1
<211> LENGTH: 2606
<212> TYPE: DNA
<213> ORGANISM: Unknown
<220> FEATURE:
<221> NAME/KEY: CDS
<222> LOCATION: (171)...(2258)
<223> OTHER INFORMATION:
<220> FEATURE:
<221> NAME/KEY: misc_feature
<222> LOCATION: 2370
<223> OTHER INFORMATION: Fungal isolate from soil sample
<220> FEATURE:
<223> OTHER INFORMATION: n = A,T,C or G

<400> SEQUENCE: 1
caattgacga ggagtcgttg ttttcctctt tttctctctc tcccgcatcg cgcgcgtgga         60
ttgggccctt tttatctttt tctgcgatat cctcgactga gaacgacgac gacgagcacg        120
acgacgacga cacaggcgac gactgcgagg cagcccccac agccgccatg atg ctc          176
                                                     Met Leu
                                                       1 cga agt cgc cag gcc tcc aag gcc ctg agg gcc ttg ggc cag gca cgg        224
Arg Ser Arg Gln Ala Ser Lys Ala Leu Arg Ala Leu Gly Gln Ala Arg
        5                  10                  15 cac ttc acc tcg acg aca cag ccc gcc gcc gtg cag gcc ccg aga aag        272
His Phe Thr Ser Thr Thr Gln Pro Ala Ala Val Gln Ala Pro Arg Lys
```

-continued

```
              20                  25                  30
gtc gcc tcc gga cag cgg aat caa gct acc gcc gcg acg gcc acc tct      320
Val Ala Ser Gly Gln Arg Asn Gln Ala Thr Ala Ala Thr Ala Thr Ser
 35                  40                  45                  50 gcc gca ccc aat gtc cgc gcc acg ccg agt cct gcc ttc aat gcg gag      368
Ala Ala Pro Asn Val Arg Ala Thr Pro Ser Pro Ala Phe Asn Ala Glu
                 55                  60                  65 gag cag cag cag caa aaa cac agc cat gtc cag ccg ctg gtc aat ccc      416
Glu Gln Gln Gln Gln Lys His Ser His Val Gln Pro Leu Val Asn Pro
         70                  75                  80 cag aag agc gac atg gat gag tcg ttc atc ggc aag acg ggc ggc gaa      464
Gln Lys Ser Asp Met Asp Glu Ser Phe Ile Gly Lys Thr Gly Gly Glu
     85                  90                  95 atc ttt cac gaa atg atg ctg aga caa ggc gtc aag cac atc ttt gga      512
Ile Phe His Glu Met Met Leu Arg Gln Gly Val Lys His Ile Phe Gly
100                 105                 110 tac ccc ggc ggc gcc atc ttg ccc gtc ttc gat gcc atc tac aac tca      560
Tyr Pro Gly Gly Ala Ile Leu Pro Val Phe Asp Ala Ile Tyr Asn Ser
115                 120                 125                 130 aaa cac ttc gac ttc atc ctg ccc aga cac gag cag ggc gcc ggc cac      608
Lys His Phe Asp Phe Ile Leu Pro Arg His Glu Gln Gly Ala Gly His
                135                 140                 145 atg gcc gag ggc tac gcc cgc gcg tcc ggc aag ccc ggc gtc gtc ctc      656
Met Ala Glu Gly Tyr Ala Arg Ala Ser Gly Lys Pro Gly Val Val Leu
        150                 155                 160 gtc acc tcg ggc ccc ggc gcc acc aac gtc gtg acc cca atg cag gac      704
Val Thr Ser Gly Pro Gly Ala Thr Asn Val Val Thr Pro Met Gln Asp
    165                 170                 175 gcc ctg tcc gac ggc acg cca ctc gtc gtc ttt tgc ggc cag gtc ccg      752
Ala Leu Ser Asp Gly Thr Pro Leu Val Val Phe Cys Gly Gln Val Pro
180                 185                 190 acc tcg gcc atc ggc agc gat gcc ttc cag gag gcc gac gtc gtc ggc      800
Thr Ser Ala Ile Gly Ser Asp Ala Phe Gln Glu Ala Asp Val Val Gly
195                 200                 205                 210 atc tcc cgc gcc tgc acc aag tgg aac gtc atg gtc aag aac gtc gcg      848
Ile Ser Arg Ala Cys Thr Lys Trp Asn Val Met Val Lys Asn Val Ala
                215                 220                 225 gag ctg ccg cgg aga atc aac gag gcc ttt gag att gcc acg agc ggt      896
Glu Leu Pro Arg Arg Ile Asn Glu Ala Phe Glu Ile Ala Thr Ser Gly
        230                 235                 240 cgc ccc ggc ccc gtc ctc gtc gac ctg ccc aag gac gtc acc gcc ggc      944
Arg Pro Gly Pro Val Leu Val Asp Leu Pro Lys Asp Val Thr Ala Gly
    245                 250                 255 atc ctg agg aga gcc atc ccc acg gag acg gcc ctg ccc gcg ctg ccg      992
Ile Leu Arg Arg Ala Ile Pro Thr Glu Thr Ala Leu Pro Ala Leu Pro
260                 265                 270 agc gcc gcc tcg cgc gcc gcc atg gag tcg agc cgg aaa cac ctc gag     1040
Ser Ala Ala Ser Arg Ala Ala Met Glu Ser Ser Arg Lys His Leu Glu
275                 280                 285                 290 cac acc atc aag cgc gtc gcc gac ctc gtc aac aag gcc aag cag cca     1088
His Thr Ile Lys Arg Val Ala Asp Leu Val Asn Lys Ala Lys Gln Pro
                295                 300                 305 gtc atc tac gcc ggc cag ggc atc atc cag tcc gag ggc ggg ccc gag     1136
Val Ile Tyr Ala Gly Gln Gly Ile Ile Gln Ser Glu Gly Gly Pro Glu
        310                 315                 320 ctc ctc aag gag ctg gcc gac aag gcc tcc atc ccc gtc acc acg acc     1184
Leu Leu Lys Glu Leu Ala Asp Lys Ala Ser Ile Pro Val Thr Thr Thr
    325                 330                 335 ctc cag ggc ctc ggc ggc ttc gac gag ctc gac gag aag tcg ctg cac     1232
```

```
Leu Gln Gly Leu Gly Gly Phe Asp Glu Leu Asp Glu Lys Ser Leu His
        340                 345                 350 atg ctc ggc atg cac ggc tcg gcc tac gcc aac atg gcc atg cag gag      1280
Met Leu Gly Met His Gly Ser Ala Tyr Ala Asn Met Ala Met Gln Glu
355                 360                 365                 370 gcc gac ctc atc atc gcc ctc ggc gcg cgc ttc gac gac cgc gtc acc      1328
Ala Asp Leu Ile Ile Ala Leu Gly Ala Arg Phe Asp Asp Arg Val Thr
                375                 380                 385 ctc aac gtg gcc aag ttc gcg cct ggc gcg agg gcc gcc gcg gcc gag      1376
Leu Asn Val Ala Lys Phe Ala Pro Gly Ala Arg Ala Ala Ala Ala Glu
            390                 395                 400 aag cgc ggc ggc atc gtc cac ttc gag gtg atg ccc aag aac atc aac      1424
Lys Arg Gly Gly Ile Val His Phe Glu Val Met Pro Lys Asn Ile Asn
        405                 410                 415 aag gtg gtg cag gcc acc gag gcc gtc gag ggc aac gtc ggc agc aac      1472
Lys Val Val Gln Ala Thr Glu Ala Val Glu Gly Asn Val Gly Ser Asn
420                 425                 430 ctc aag ctc ctg ctg ccc gag gtg cag gcc aag acg atg gac gac cgc      1520
Leu Lys Leu Leu Leu Pro Glu Val Gln Ala Lys Thr Met Asp Asp Arg
435                 440                 445                 450 aag gag tgg ttc ggc aag atc aac gag tgg aag aag aag tgg ccg ctg      1568
Lys Glu Trp Phe Gly Lys Ile Asn Glu Trp Lys Lys Lys Trp Pro Leu
                455                 460                 465 tcg cac tac gag cgt gcg gag cgc cac ggg ctc atc aag ccg cag acc      1616
Ser His Tyr Glu Arg Ala Glu Arg His Gly Leu Ile Lys Pro Gln Thr
                470                 475                 480 ctc atc gag gag ctg agc aag ctg acg gcg gac cgc aag gac aag acg      1664
Leu Ile Glu Glu Leu Ser Lys Leu Thr Ala Asp Arg Lys Asp Lys Thr
            485                 490                 495 tac att gcc acc ggc gtc gga cag cac cag atg tgg acg gcc cag cac      1712
Tyr Ile Ala Thr Gly Val Gly Gln His Gln Met Trp Thr Ala Gln His
        500                 505                 510 ttc cgg tgg agg cac ccg cgc agc atg atc acg tcg ggt ggt ctc ggc      1760
Phe Arg Trp Arg His Pro Arg Ser Met Ile Thr Ser Gly Gly Leu Gly
515                 520                 525                 530 act atg ggc ttc ggt ctg ccg gct gcc atc ggt gcc aag gtc gcg cag      1808
Thr Met Gly Phe Gly Leu Pro Ala Ala Ile Gly Ala Lys Val Ala Gln
                535                 540                 545 ccg gac gcc ctc gtc ttc gat atc gat ggc gac gcg tca ttt ggc atg      1856
Pro Asp Ala Leu Val Phe Asp Ile Asp Gly Asp Ala Ser Phe Gly Met
                550                 555                 560 acc ctg acg gag ctg gcc acg gcg gcg cag ttc aac att ggc gtc aag      1904
Thr Leu Thr Glu Leu Ala Thr Ala Ala Gln Phe Asn Ile Gly Val Lys
            565                 570                 575 gtc att gtc ctc aac aac gag gag cag ggc atg gta acg cag tgg cag      1952
Val Ile Val Leu Asn Asn Glu Glu Gln Gly Met Val Thr Gln Trp Gln
580                 585                 590 aac ctc ttc tac gag gac cgc tac gcg cac acg cac cag gtc aac cct      2000
Asn Leu Phe Tyr Glu Asp Arg Tyr Ala His Thr His Gln Val Asn Pro
595                 600                 605                 610 gat ttc atg aag ctg gcc gag tcg atg cgc gtc cag ggc cgg cga tgc      2048
Asp Phe Met Lys Leu Ala Glu Ser Met Arg Val Gln Gly Arg Arg Cys
                615                 620                 625 gtg gac ccc gag gac gtg gtc gac agc ctg aag tgg ctg atc aac act      2096
Val Asp Pro Glu Asp Val Val Asp Ser Leu Lys Trp Leu Ile Asn Thr
                630                 635                 640 gac ggc ccg gcc ctg ctg gag gtt gtc acg gac aag aag gtg ccc gtc      2144
Asp Gly Pro Ala Leu Leu Glu Val Val Thr Asp Lys Lys Val Pro Val
            645                 650                 655
```

```
ctg ccc atg gtg ccg gcg ggc tcg gcc ctg cac gag ttt ttg gtg ttt      2192
Leu Pro Met Val Pro Ala Gly Ser Ala Leu His Glu Phe Leu Val Phe
    660             665                 670 gac gga gaa aag gac aag aag cga cga gag ctg atg cgg gaa agg acc      2240
Asp Gly Glu Lys Asp Lys Lys Arg Arg Glu Leu Met Arg Glu Arg Thr
675                 680                 685                 690 tcg ggc ctg cac ggc tag ccgcagcaca cggggcggat tagcagcacc             2288
Ser Gly Leu His Gly *
                695 cgacgacggg catccatcca tcaatcatct tctagtcatg ttcttttcat acctcttact    2348 ggcggagttt tgtgcagtta angcaaatcc gggcgcgaag cacaaaaagt tggaggagga    2408 gcagcgccga acggcggcgc ggtggtagca caggggtggc aatgtgacgg cgggtcgaag    2468 agcccgggca tggcagagta gggcggttgg ttcccatgag gcgagcgagc cgcgcgcggg    2528 cttgcggacg gacacaaaca aacaatgaat gaccatttt ccgagacgtg aaaaaaaaaa     2588 aaaaaaaaaa aaaaaaaa                                                  2606

<210> SEQ ID NO 2
<211> LENGTH: 2085
<212> TYPE: DNA
<213> ORGANISM: Unknown
<220> FEATURE:
<221> NAME/KEY: CDS
<222> LOCATION: (1)...(2085)
<223> OTHER INFORMATION: Fungal isolate from soil sample

<400> SEQUENCE: 2 atg ctc cga agt cgc cag gcc tcc aag gcc ctg agg gcc ttg ggc cag       48
Met Leu Arg Ser Arg Gln Ala Ser Lys Ala Leu Arg Ala Leu Gly Gln
1               5                   10                  15 gca cgg cac ttc acc tcg acg aca cag ccc gcc gcc gtg cag gcc ccg       96
Ala Arg His Phe Thr Ser Thr Thr Gln Pro Ala Ala Val Gln Ala Pro
                20                  25                  30 aga aag gtc gcc tcc gga cag cgg aat caa gct acc gcc gcg acg gcc      144
Arg Lys Val Ala Ser Gly Gln Arg Asn Gln Ala Thr Ala Ala Thr Ala
            35                  40                  45 acc tct gcc gca ccc aat gtc cgc gcc acg ccg agt cct gcc ttc aat      192
Thr Ser Ala Ala Pro Asn Val Arg Ala Thr Pro Ser Pro Ala Phe Asn
        50                  55                  60 gcg gag gag cag cag cag caa aaa cac agc cat gtc cag ccg ctg gtc      240
Ala Glu Glu Gln Gln Gln Gln Lys His Ser His Val Gln Pro Leu Val
65                  70                  75                  80 aat ccc cag aag agc gac atg gat gag tcg ttc atc ggc aag acg ggc      288
Asn Pro Gln Lys Ser Asp Met Asp Glu Ser Phe Ile Gly Lys Thr Gly
                85                  90                  95 ggc gaa atc ttt cac gaa atg atg ctg aga caa ggc gtc aag cac atc      336
Gly Glu Ile Phe His Glu Met Met Leu Arg Gln Gly Val Lys His Ile
                100                 105                 110 ttt gga tac ccc ggc ggc gcc atc ttg ccc gtc ttc gat gcc atc tac      384
Phe Gly Tyr Pro Gly Gly Ala Ile Leu Pro Val Phe Asp Ala Ile Tyr
            115                 120                 125 aac tca aaa cac ttc gac ttc atc ctg ccc aga cac gag cag ggc gcc      432
Asn Ser Lys His Phe Asp Phe Ile Leu Pro Arg His Glu Gln Gly Ala
        130                 135                 140 ggc cac atg gcc gag ggc tac gcc cgc gcg tcc ggc aag ccc ggc gtc      480
Gly His Met Ala Glu Gly Tyr Ala Arg Ala Ser Gly Lys Pro Gly Val
145                 150                 155                 160 gtc ctc gtc acc tcg ggc ccc ggc gcc acc aac gtc gtg acc cca atg      528
Val Leu Val Thr Ser Gly Pro Gly Ala Thr Asn Val Val Thr Pro Met
                165                 170                 175
```

```
cag gac gcc ctg tcc gac ggc acg cca ctc gtc gtc ttt tgc ggc cag        576
Gln Asp Ala Leu Ser Asp Gly Thr Pro Leu Val Val Phe Cys Gly Gln
        180                 185                 190 gtc ccg acc tcg gcc atc ggc agc gat gcc ttc cag gag gcc gac gtc        624
Val Pro Thr Ser Ala Ile Gly Ser Asp Ala Phe Gln Glu Ala Asp Val
            195                 200                 205 gtc ggc atc tcc cgc gcc tgc acc aag tgg aac gtc atg gtc aag aac        672
Val Gly Ile Ser Arg Ala Cys Thr Lys Trp Asn Val Met Val Lys Asn
    210                 215                 220 gtc gcg gag ctg ccg cgg aga atc aac gag gcc ttt gag att gcc acg        720
Val Ala Glu Leu Pro Arg Arg Ile Asn Glu Ala Phe Glu Ile Ala Thr
225                 230                 235                 240 agc ggt cgc ccc ggc ccc gtc ctc gtc gac ctg ccc aag gac gtc acc        768
Ser Gly Arg Pro Gly Pro Val Leu Val Asp Leu Pro Lys Asp Val Thr
                245                 250                 255 gcc ggc atc ctg agg aga gcc atc ccc acg gag acg gcc ctg ccc gcg        816
Ala Gly Ile Leu Arg Arg Ala Ile Pro Thr Glu Thr Ala Leu Pro Ala
            260                 265                 270 ctg ccg agc gcc gcc tcg cgc gcc gcc atg gag tcg agc cgg aaa cac        864
Leu Pro Ser Ala Ala Ser Arg Ala Ala Met Glu Ser Ser Arg Lys His
        275                 280                 285 ctc gag cac acc atc aag cgc gtc gcc gac ctc gtc aac aag gcc aag        912
Leu Glu His Thr Ile Lys Arg Val Ala Asp Leu Val Asn Lys Ala Lys
    290                 295                 300 cag cca gtc atc tac gcc ggc cag ggc atc atc cag tcc gag ggc ggg        960
Gln Pro Val Ile Tyr Ala Gly Gln Gly Ile Ile Gln Ser Glu Gly Gly
305                 310                 315                 320 ccc gag ctc ctc aag gag ctg gcc gac aag gcc tcc atc ccc gtc acc       1008
Pro Glu Leu Leu Lys Glu Leu Ala Asp Lys Ala Ser Ile Pro Val Thr
                325                 330                 335 acg acc ctc cag ggc ctc ggc ggc ttc gac gag ctc gac gag aag tcg       1056
Thr Thr Leu Gln Gly Leu Gly Gly Phe Asp Glu Leu Asp Glu Lys Ser
            340                 345                 350 ctg cac atg ctc ggc atg cac ggc tcg gcc tac gcc aac atg gcc atg       1104
Leu His Met Leu Gly Met His Gly Ser Ala Tyr Ala Asn Met Ala Met
        355                 360                 365 cag gag gcc gac ctc atc atc gcc ctc ggc gcg cgc ttc gac gac cgc       1152
Gln Glu Ala Asp Leu Ile Ile Ala Leu Gly Ala Arg Phe Asp Asp Arg
    370                 375                 380 gtc acc ctc aac gtg gcc aag ttc gcg cct ggc gcg agg gcc gcc gcg       1200
Val Thr Leu Asn Val Ala Lys Phe Ala Pro Gly Ala Arg Ala Ala Ala
385                 390                 395                 400 gcc gag aag cgc ggc ggc atc gtc cac ttc gag gtg atg ccc aag aac       1248
Ala Glu Lys Arg Gly Gly Ile Val His Phe Glu Val Met Pro Lys Asn
                405                 410                 415 atc aac aag gtg gtg cag gcc acc gag gcc gtc gag ggc aac gtc ggc       1296
Ile Asn Lys Val Val Gln Ala Thr Glu Ala Val Glu Gly Asn Val Gly
            420                 425                 430 agc aac ctc aag ctc ctg ctg ccc gag gtg cag gcc aag acg atg gac       1344
Ser Asn Leu Lys Leu Leu Leu Pro Glu Val Gln Ala Lys Thr Met Asp
        435                 440                 445 gac cgc aag gag tgg ttc ggc aag atc aac gag tgg aag aag aag tgg       1392
Asp Arg Lys Glu Trp Phe Gly Lys Ile Asn Glu Trp Lys Lys Lys Trp
    450                 455                 460 ccg ctg tcg cac tac gag cgt gcg gag cgc cac ggg ctc atc aag ccg       1440
Pro Leu Ser His Tyr Glu Arg Ala Glu Arg His Gly Leu Ile Lys Pro
465                 470                 475                 480 cag acc ctc atc gag gag ctg agc aag ctg acg gcg gac cgc aag gac       1488
Gln Thr Leu Ile Glu Glu Leu Ser Lys Leu Thr Ala Asp Arg Lys Asp
```

-continued

```
            485                 490                 495
aag acg tac att gcc acc ggc gtc gga cag cac cag atg tgg acg gcc      1536
Lys Thr Tyr Ile Ala Thr Gly Val Gly Gln His Gln Met Trp Thr Ala
        500                 505                 510 cag cac ttc cgg tgg agg cac ccg cgc agc atg atc acg tcg ggt ggt      1584
Gln His Phe Arg Trp Arg His Pro Arg Ser Met Ile Thr Ser Gly Gly
    515                 520                 525 ctc ggc act atg ggc ttc ggt ctg ccg gct gcc atc ggt gcc aag gtc      1632
Leu Gly Thr Met Gly Phe Gly Leu Pro Ala Ala Ile Gly Ala Lys Val
530                 535                 540 gcg cag ccg gac gcc ctc gtc ttc gat atc gat ggc gac gcg tca ttt      1680
Ala Gln Pro Asp Ala Leu Val Phe Asp Ile Asp Gly Asp Ala Ser Phe
545                 550                 555                 560 ggc atg acc ctg acg gag ctg gcc acg gcg gcg cag ttc aac att ggc      1728
Gly Met Thr Leu Thr Glu Leu Ala Thr Ala Ala Gln Phe Asn Ile Gly
            565                 570                 575 gtc aag gtc att gtc ctc aac aac gag gag cag ggc atg gta acg cag      1776
Val Lys Val Ile Val Leu Asn Asn Glu Glu Gln Gly Met Val Thr Gln
        580                 585                 590 tgg cag aac ctc ttc tac gag gac cgc tac gcg cac acg cac cag gtc      1824
Trp Gln Asn Leu Phe Tyr Glu Asp Arg Tyr Ala His Thr His Gln Val
    595                 600                 605 aac cct gat ttc atg aag ctg gcc gag tcg atg cgc gtc cag ggc cgg      1872
Asn Pro Asp Phe Met Lys Leu Ala Glu Ser Met Arg Val Gln Gly Arg
610                 615                 620 cga tgc gtg gac ccc gag gac gtg gtc gac agc ctg aag tgg ctg atc      1920
Arg Cys Val Asp Pro Glu Asp Val Val Asp Ser Leu Lys Trp Leu Ile
625                 630                 635                 640 aac act gac ggc ccg gcc ctg ctg gag gtt gtc acg gac aag aag gtg      1968
Asn Thr Asp Gly Pro Ala Leu Leu Glu Val Val Thr Asp Lys Lys Val
            645                 650                 655 ccc gtc ctg ccc atg gtg ccg gcg ggc tcg gcc ctg cac gag ttt ttg      2016
Pro Val Leu Pro Met Val Pro Ala Gly Ser Ala Leu His Glu Phe Leu
        660                 665                 670 gtg ttt gac gga gaa aag gac aag aag cga cga gag ctg atg cgg gaa      2064
Val Phe Asp Gly Glu Lys Asp Lys Lys Arg Arg Glu Leu Met Arg Glu
    675                 680                 685 agg acc tcg ggc ctg cac ggc                                          2085
Arg Thr Ser Gly Leu His Gly
    690                 695

<210> SEQ ID NO 3
<211> LENGTH: 695
<212> TYPE: PRT
<213> ORGANISM: Unknown
<220> FEATURE:
<223> OTHER INFORMATION: Fungal isolate from soil sample

<400> SEQUENCE: 3

Met Leu Arg Ser Arg Gln Ala Ser Lys Ala Leu Arg Ala Leu Gly Gln
 1               5                  10                  15

Ala Arg His Phe Thr Ser Thr Thr Gln Pro Ala Ala Val Gln Ala Pro
            20                  25                  30

Arg Lys Val Ala Ser Gly Gln Arg Asn Gln Ala Thr Ala Ala Thr Ala
        35                  40                  45

Thr Ser Ala Ala Pro Asn Val Arg Ala Thr Pro Ser Pro Ala Phe Asn
    50                  55                  60

Ala Glu Glu Gln Gln Gln Gln Lys His Ser His Val Gln Pro Leu Val
65                  70                  75                  80
```

-continued

```
Asn Pro Gln Lys Ser Asp Met Asp Glu Ser Phe Ile Gly Lys Thr Gly
            85                  90                  95
Gly Glu Ile Phe His Glu Met Met Leu Arg Gln Gly Val Lys His Ile
        100                 105                 110
Phe Gly Tyr Pro Gly Gly Ala Ile Leu Pro Val Phe Asp Ala Ile Tyr
    115                 120                 125
Asn Ser Lys His Phe Asp Phe Ile Leu Pro Arg His Glu Gln Gly Ala
130                 135                 140
Gly His Met Ala Glu Gly Tyr Ala Arg Ala Ser Gly Lys Pro Gly Val
145                 150                 155                 160
Val Leu Val Thr Ser Gly Pro Gly Ala Thr Asn Val Val Thr Pro Met
                165                 170                 175
Gln Asp Ala Leu Ser Asp Gly Thr Pro Leu Val Val Phe Cys Gly Gln
            180                 185                 190
Val Pro Thr Ser Ala Ile Gly Ser Asp Ala Phe Gln Glu Ala Asp Val
        195                 200                 205
Val Gly Ile Ser Arg Ala Cys Thr Lys Trp Asn Val Met Val Lys Asn
    210                 215                 220
Val Ala Glu Leu Pro Arg Arg Ile Asn Glu Ala Phe Glu Ile Ala Thr
225                 230                 235                 240
Ser Gly Arg Pro Gly Pro Val Leu Val Asp Leu Pro Lys Asp Val Thr
                245                 250                 255
Ala Gly Ile Leu Arg Arg Ala Ile Pro Thr Glu Thr Ala Leu Pro Ala
            260                 265                 270
Leu Pro Ser Ala Ala Ser Arg Ala Ala Met Glu Ser Ser Arg Lys His
        275                 280                 285
Leu Glu His Thr Ile Lys Arg Val Ala Asp Leu Val Asn Lys Ala Lys
    290                 295                 300
Gln Pro Val Ile Tyr Ala Gly Gln Gly Ile Ile Gln Ser Glu Gly Gly
305                 310                 315                 320
Pro Glu Leu Leu Lys Glu Leu Ala Asp Lys Ala Ser Ile Pro Val Thr
                325                 330                 335
Thr Thr Leu Gln Gly Leu Gly Gly Phe Asp Glu Leu Asp Glu Lys Ser
            340                 345                 350
Leu His Met Leu Gly Met His Gly Ser Ala Tyr Ala Asn Met Ala Met
        355                 360                 365
Gln Glu Ala Asp Leu Ile Ile Ala Leu Gly Ala Arg Phe Asp Asp Arg
    370                 375                 380
Val Thr Leu Asn Val Ala Lys Phe Ala Pro Gly Ala Arg Ala Ala Ala
385                 390                 395                 400
Ala Glu Lys Arg Gly Gly Ile Val His Phe Glu Val Met Pro Lys Asn
                405                 410                 415
Ile Asn Lys Val Val Gln Ala Thr Glu Ala Val Glu Gly Asn Val Gly
            420                 425                 430
Ser Asn Leu Lys Leu Leu Pro Glu Val Gln Ala Lys Thr Met Asp
        435                 440                 445
Asp Arg Lys Glu Trp Phe Gly Lys Ile Asn Glu Trp Lys Lys Lys Trp
    450                 455                 460
Pro Leu Ser His Tyr Glu Arg Ala Glu Arg His Gly Leu Ile Lys Pro
465                 470                 475                 480
Gln Thr Leu Ile Glu Glu Leu Ser Lys Leu Thr Ala Asp Arg Lys Asp
                485                 490                 495
Lys Thr Tyr Ile Ala Thr Gly Val Gly Gln His Gln Met Trp Thr Ala
```

-continued

```
                500             505             510
Gln His Phe Arg Trp Arg His Pro Arg Ser Met Ile Thr Ser Gly Gly
            515                 520                 525

Leu Gly Thr Met Gly Phe Gly Leu Pro Ala Ala Ile Gly Ala Lys Val
        530                 535                 540

Ala Gln Pro Asp Ala Leu Val Phe Asp Ile Asp Gly Asp Ala Ser Phe
545                 550                 555                 560

Gly Met Thr Leu Thr Glu Leu Ala Thr Ala Ala Gln Phe Asn Ile Gly
                565                 570                 575

Val Lys Val Ile Val Leu Asn Asn Glu Glu Gln Gly Met Val Thr Gln
                580                 585                 590

Trp Gln Asn Leu Phe Tyr Glu Asp Arg Tyr Ala His Thr His Gln Val
            595                 600                 605

Asn Pro Asp Phe Met Lys Leu Ala Glu Ser Met Arg Val Gln Gly Arg
        610                 615                 620

Arg Cys Val Asp Pro Glu Asp Val Val Asp Ser Leu Lys Trp Leu Ile
625                 630                 635                 640

Asn Thr Asp Gly Pro Ala Leu Leu Glu Val Val Thr Asp Lys Lys Val
                645                 650                 655

Pro Val Leu Pro Met Val Pro Ala Gly Ser Ala Leu His Glu Phe Leu
            660                 665                 670

Val Phe Asp Gly Glu Lys Asp Lys Lys Arg Arg Glu Leu Met Arg Glu
        675                 680                 685

Arg Thr Ser Gly Leu His Gly
        690                 695

<210> SEQ ID NO 4
<211> LENGTH: 687
<212> TYPE: PRT
<213> ORGANISM: Saccharomyces cerevisiae

<400> SEQUENCE: 4

Met Ile Arg Gln Ser Thr Leu Lys Asn Phe Ala Ile Lys Arg Cys Phe
1               5                   10                  15

Gln His Ile Ala Tyr Arg Asn Thr Pro Ala Met Arg Ser Val Ala Leu
            20                  25                  30

Ala Gln Arg Phe Tyr Ser Ser Ser Arg Tyr Ser Ala Ser Pro
        35                  40                  45

Leu Pro Ala Ser Lys Arg Pro Glu Pro Ala Pro Ser Phe Asn Val Asp
    50                  55                  60

Pro Leu Glu Gln Pro Ala Glu Pro Ser Lys Leu Ala Lys Lys Leu Arg
65                  70                  75                  80

Ala Glu Pro Asp Met Asp Thr Ser Phe Val Gly Leu Thr Gly Gly Gln
                85                  90                  95

Ile Phe Asn Glu Met Met Ser Arg Gln Asn Val Asp Thr Val Phe Gly
            100                 105                 110

Tyr Pro Gly Gly Ala Ile Leu Pro Val Tyr Asp Ala Ile His Asn Ser
        115                 120                 125

Asp Lys Phe Asn Phe Val Leu Pro Lys His Glu Gln Gly Ala Gly His
    130                 135                 140

Met Ala Glu Gly Tyr Ala Arg Ala Ser Gly Lys Pro Gly Val Val Leu
145                 150                 155                 160

Val Thr Ser Gly Pro Gly Ala Thr Asn Val Val Thr Pro Met Ala Asp
                165                 170                 175
```

-continued

```
Ala Phe Ala Asp Gly Ile Pro Met Val Val Phe Thr Gly Gln Val Pro
            180                 185                 190

Thr Ser Ala Ile Gly Thr Asp Ala Phe Gln Glu Ala Asp Val Val Gly
            195                 200                 205

Ile Ser Arg Ser Cys Thr Lys Trp Asn Val Met Val Lys Ser Val Glu
210                 215                 220

Glu Leu Pro Leu Arg Ile Asn Glu Ala Phe Glu Ile Ala Thr Ser Gly
225                 230                 235                 240

Arg Pro Gly Pro Val Leu Val Asp Leu Pro Lys Asp Val Thr Ala Ala
                245                 250                 255

Ile Leu Arg Asn Pro Ile Pro Thr Lys Thr Thr Leu Pro Ser Asn Ala
            260                 265                 270

Leu Asn Gln Leu Thr Ser Arg Ala Gln Asp Glu Phe Val Met Gln Ser
            275                 280                 285

Ile Asn Lys Ala Ala Asp Leu Ile Asn Leu Ala Lys Lys Pro Val Leu
    290                 295                 300

Tyr Val Gly Ala Gly Ile Leu Asn His Ala Asp Gly Pro Arg Leu Leu
305                 310                 315                 320

Lys Glu Leu Ser Asp Arg Ala Gln Ile Pro Val Thr Thr Thr Leu Gln
                325                 330                 335

Gly Leu Gly Ser Phe Asp Gln Glu Asp Pro Lys Ser Leu Asp Met Leu
            340                 345                 350

Gly Met His Gly Cys Ala Thr Ala Asn Leu Ala Val Gln Asn Ala Asp
            355                 360                 365

Leu Ile Ile Ala Val Gly Ala Arg Phe Asp Asp Arg Val Thr Gly Asn
    370                 375                 380

Ile Ser Lys Phe Ala Pro Glu Ala Arg Arg Ala Ala Glu Gly Arg
385                 390                 395                 400

Gly Gly Ile Ile His Phe Glu Val Ser Pro Lys Asn Ile Asn Lys Val
                405                 410                 415

Val Gln Thr Gln Ile Ala Val Glu Gly Asp Ala Thr Thr Asn Leu Gly
            420                 425                 430

Lys Met Met Ser Lys Ile Phe Pro Val Lys Glu Arg Ser Glu Trp Phe
            435                 440                 445

Ala Gln Ile Asn Lys Trp Lys Lys Glu Tyr Pro Tyr Ala Tyr Met Glu
    450                 455                 460

Glu Thr Pro Gly Ser Lys Ile Lys Pro Gln Thr Val Ile Lys Lys Leu
465                 470                 475                 480

Ser Lys Val Ala Asn Asp Thr Gly Arg His Val Ile Val Thr Thr Gly
                485                 490                 495

Val Gly Gln His Gln Met Trp Ala Ala Gln His Trp Thr Trp Arg Asn
            500                 505                 510

Pro His Thr Phe Ile Thr Ser Gly Gly Leu Gly Thr Met Gly Tyr Gly
            515                 520                 525

Leu Pro Ala Ala Ile Gly Ala Gln Val Ala Lys Pro Glu Ser Leu Val
    530                 535                 540

Ile Asp Ile Asp Gly Asp Ala Ser Phe Asn Met Thr Leu Thr Glu Leu
545                 550                 555                 560

Ser Ser Ala Val Gln Ala Gly Thr Pro Val Lys Ile Leu Ile Leu Asn
                565                 570                 575

Asn Glu Glu Gln Gly Met Val Thr Gln Trp Gln Ser Leu Phe Tyr Glu
            580                 585                 590

His Arg Tyr Ser His Thr His Gln Leu Asn Pro Asp Phe Ile Lys Leu
```

```
                 595                 600                 605
Ala Glu Ala Met Gly Leu Lys Gly Leu Arg Val Lys Lys Gln Glu Glu
            610                 615                 620

Leu Asp Ala Lys Leu Lys Glu Phe Val Ser Thr Lys Gly Pro Val Leu
625                 630                 635                 640

Leu Glu Val Glu Val Asp Lys Lys Val Pro Val Leu Pro Met Val Ala
                645                 650                 655

Gly Gly Ser Gly Leu Asp Glu Phe Ile Asn Phe Asp Pro Glu Val Glu
            660                 665                 670

Arg Gln Gln Thr Glu Leu Arg His Lys Arg Thr Gly Gly Lys His
            675                 680                 685

<210> SEQ ID NO 5
<211> LENGTH: 682
<212> TYPE: PRT
<213> ORGANISM: Magnaporthe grisea

<400> SEQUENCE: 5

Met Leu Arg Thr Val Gly Arg Lys Ala Leu Arg Gly Ser Ser Lys Gly
1               5                   10                  15

Cys Ser Arg Thr Ile Ser Thr Leu Lys Pro Ala Thr Ala Thr Ile Ala
            20                  25                  30

Lys Pro Gly Ser Arg Thr Leu Ser Thr Pro Ala Thr Ala Thr Ala Thr
        35                  40                  45

Ala Pro Arg Thr Lys Pro Ser Ala Ser Phe Asn Ala Arg Arg Asp Pro
    50                  55                  60

Gln Pro Leu Val Asn Pro Arg Ser Gly Glu Ala Asp Glu Ser Phe Ile
65                  70                  75                  80

Gly Lys Thr Gly Gly Glu Ile Phe His Glu Met Met Leu Arg Gln Asn
                85                  90                  95

Val Lys His Ile Phe Gly Tyr Pro Gly Gly Ala Ile Leu Pro Val Phe
            100                 105                 110

Asp Ala Ile Tyr Asn Ser Lys His Ile Asp Phe Val Leu Pro Lys His
        115                 120                 125

Glu Gln Gly Ala Gly His Met Ala Glu Gly Tyr Ala Arg Ala Ser Gly
    130                 135                 140

Lys Pro Gly Val Val Leu Val Thr Ser Gly Pro Gly Ala Thr Asn Val
145                 150                 155                 160

Ile Thr Pro Met Ala Asp Ala Leu Ala Asp Gly Thr Pro Leu Val Val
                165                 170                 175

Phe Ser Gly Gln Val Val Thr Ser Asp Ile Gly Ser Asp Ala Phe Gln
            180                 185                 190

Glu Ala Asp Val Ile Gly Ile Ser Arg Ser Cys Thr Lys Trp Asn Val
        195                 200                 205

Met Val Lys Ser Ala Asp Glu Leu Pro Arg Arg Ile Asn Glu Ala Phe
    210                 215                 220

Glu Ile Ala Thr Ser Gly Arg Pro Gly Pro Val Leu Val Asp Pro Ala
225                 230                 235                 240

Lys Asp Val Thr Ala Ser Val Leu Arg Arg Ala Ile Pro Thr Glu Thr
                245                 250                 255

Ser Ile Pro Ser Ile Ser Ala Ala Arg Ala Val Gln Glu Ala Gly
            260                 265                 270

Arg Lys Gln Leu Glu His Ser Ile Lys Arg Val Ala Asp Leu Val Asn
        275                 280                 285
```

```
Ile Ala Lys Lys Pro Val Ile Tyr Ala Gly Gln Gly Val Ile Leu Ser
290                 295                 300
Glu Gly Gly Val Glu Leu Leu Lys Ala Leu Ala Asp Lys Ala Ser Ile
305                 310                 315                 320
Pro Val Thr Thr Thr Leu His Gly Leu Gly Ala Phe Asp Glu Leu Asp
                325                 330                 335
Glu Lys Ala Leu His Met Leu Gly Met His Gly Ser Ala Tyr Ala Asn
                340                 345                 350
Met Ser Met Gln Glu Ala Asp Leu Ile Ile Ala Leu Gly Gly Arg Phe
                355                 360                 365
Asp Asp Arg Val Thr Gly Ser Ile Pro Lys Phe Ala Pro Ala Ala Lys
370                 375                 380
Leu Ala Ala Ala Glu Gly Arg Gly Gly Ile Val His Phe Glu Ile Met
385                 390                 395                 400
Pro Lys Asn Ile Asn Lys Val Val Gln Ala Thr Glu Ala Ile Glu Gly
                405                 410                 415
Asp Val Ala Ser Asn Leu Lys Leu Leu Leu Pro Lys Ile Glu Gln Arg
                420                 425                 430
Ser Met Thr Asp Arg Lys Glu Trp Phe Asp Gln Ile Lys Glu Trp Lys
                435                 440                 445
Glu Lys Trp Pro Leu Ser His Tyr Glu Arg Ala Glu Arg Ser Gly Leu
450                 455                 460
Ile Lys Pro Gln Thr Leu Ile Glu Glu Leu Ser Asn Leu Thr Ala Asp
465                 470                 475                 480
Arg Lys Asp Met Thr Tyr Ile Thr Thr Gly Val Gly Gln His Gln Met
                485                 490                 495
Trp Thr Ala Gln His Phe Arg Trp Arg His Pro Arg Ser Met Ile Thr
                500                 505                 510
Ser Gly Gly Leu Gly Thr Met Gly Tyr Gly Leu Pro Ala Ala Ile Gly
                515                 520                 525
Ala Lys Val Ala Arg Pro Asp Ala Leu Val Ile Asp Ile Asp Gly Asp
530                 535                 540
Ala Ser Phe Asn Met Thr Leu Thr Glu Leu Ser Thr Ala Ala Gln Phe
545                 550                 555                 560
Asn Ile Gly Val Lys Val Ile Val Leu Asn Asn Glu Glu Gln Gly Met
                565                 570                 575
Val Thr Gln Trp Gln Asn Leu Phe Tyr Glu Asp Arg Tyr Ser His Thr
                580                 585                 590
His Gln Arg Asn Pro Asp Phe Met Lys Leu Ala Asp Ala Met Asp Val
                595                 600                 605
Gln His Arg Arg Val Ser Lys Pro Asp Val Gly Asp Ala Leu Thr
                610                 615                 620
Trp Leu Ile Asn Thr Asp Gly Pro Ala Leu Leu Glu Val Met Thr Asp
625                 630                 635                 640
Lys Lys Val Pro Val Leu Pro Met Val Pro Gly Gly Asn Gly Leu His
                645                 650                 655
Glu Phe Ile Thr Phe Asp Ala Ser Lys Asp Lys Gln Arg Glu Leu
                660                 665                 670
Met Arg Ala Arg Thr Asn Gly Leu His Gly
                675                 680
```

<210> SEQ ID NO 6
<211> LENGTH: 695
<212> TYPE: PRT

<213> ORGANISM: Unknown
<220> FEATURE:
<223> OTHER INFORMATION: Fungal isolate from soil sample

<400> SEQUENCE: 6

```
Met Leu Arg Ser Arg Gln Ala Ser Lys Ala Leu Arg Ala Leu Gly Gln
 1               5                  10                  15

Ala Arg His Phe Thr Ser Thr Thr Gln Pro Ala Ala Val Gln Ala Pro
             20                  25                  30

Arg Lys Val Ala Ser Gly Gln Arg Asn Gln Ala Thr Ala Ala Thr Ala
         35                  40                  45

Thr Ser Ala Ala Pro Asn Val Arg Ala Thr Pro Ser Pro Ala Phe Asn
 50                  55                  60

Ala Glu Gln Gln Gln Gln Lys His Ser His Val Gln Pro Leu Val
 65                  70                  75                  80

Asn Pro Gln Lys Ser Asp Met Asp Glu Ser Phe Ile Gly Lys Thr Gly
                 85                  90                  95

Gly Glu Ile Phe His Glu Met Met Leu Arg Gln Gly Val Lys His Ile
                100                 105                 110

Phe Gly Tyr Pro Gly Gly Ala Ile Leu Pro Val Phe Asp Ala Ile Tyr
            115                 120                 125

Asn Ser Lys His Phe Asp Phe Ile Leu Pro Arg His Glu Gln Gly Ala
130                 135                 140

Gly His Met Ala Glu Gly Tyr Ala Arg Ala Ser Gly Lys Pro Gly Val
145                 150                 155                 160

Val Leu Val Thr Ser Gly Pro Gly Ala Thr Asn Val Val Thr Pro Met
                165                 170                 175

Gln Asp Ala Leu Ser Asp Gly Thr Pro Leu Val Val Phe Cys Gly Gln
            180                 185                 190

Val Pro Thr Ser Ala Ile Gly Ser Asp Ala Phe Gln Glu Ala Asp Val
        195                 200                 205

Val Gly Ile Ser Arg Ala Cys Thr Lys Trp Asn Val Met Val Lys Asn
    210                 215                 220

Val Ala Glu Leu Pro Arg Arg Ile Asn Glu Ala Phe Glu Ile Ala Thr
225                 230                 235                 240

Ser Gly Arg Pro Gly Pro Val Leu Val Asp Leu Pro Lys Asp Val Thr
                245                 250                 255

Ala Gly Ile Leu Arg Arg Ala Ile Pro Thr Glu Thr Ala Leu Pro Ala
            260                 265                 270

Leu Pro Ser Ala Ala Ser Arg Ala Ala Met Glu Ser Ser Arg Lys His
        275                 280                 285

Leu Glu His Thr Ile Lys Arg Val Ala Asp Leu Val Asn Lys Ala Lys
    290                 295                 300

Gln Pro Val Ile Tyr Ala Gly Gln Gly Ile Ile Gln Ser Glu Gly Gly
305                 310                 315                 320

Pro Glu Leu Leu Lys Glu Leu Ala Asp Lys Ala Ser Ile Pro Val Thr
                325                 330                 335

Thr Thr Leu Gln Gly Leu Gly Gly Phe Asp Glu Leu Asp Glu Lys Ser
            340                 345                 350

Leu His Met Leu Gly Met His Gly Ser Ala Tyr Ala Asn Met Ala Met
        355                 360                 365

Gln Glu Ala Asp Leu Ile Ile Ala Leu Gly Ala Arg Phe Asp Asp Arg
    370                 375                 380

Val Thr Leu Asn Val Ala Lys Phe Ala Pro Gly Ala Arg Ala Ala Ala
```

```
                                       -continued
385                 390                 395                 400
Ala Glu Lys Arg Gly Gly Ile Val His Phe Glu Val Met Pro Lys Asn
                405                 410                 415
Ile Asn Lys Val Val Gln Ala Thr Glu Ala Val Glu Gly Asn Val Gly
                420                 425                 430
Ser Asn Leu Lys Leu Leu Leu Pro Glu Val Gln Ala Lys Thr Met Asp
                435                 440                 445
Asp Arg Lys Glu Trp Phe Gly Lys Ile Asn Glu Trp Lys Lys Lys Trp
                450                 455                 460
Pro Leu Ser His Tyr Glu Arg Ala Glu Arg His Gly Leu Ile Lys Pro
465                 470                 475                 480
Gln Thr Leu Ile Glu Glu Leu Ser Lys Leu Thr Ala Asp Arg Lys Asp
                485                 490                 495
Lys Thr Tyr Ile Ala Thr Gly Val Gly Gln His Gln Met Trp Thr Ala
                500                 505                 510
Gln His Phe Arg Trp Arg His Pro Arg Ser Met Ile Thr Ser Gly Gly
                515                 520                 525
Leu Gly Thr Met Gly Phe Gly Leu Pro Ala Ala Ile Gly Ala Lys Val
                530                 535                 540
Ala Gln Pro Asp Ala Leu Val Phe Asp Ile Asp Gly Asp Ala Ser Phe
545                 550                 555                 560
Gly Met Thr Leu Thr Glu Leu Ala Thr Ala Ala Gln Phe Asn Ile Gly
                565                 570                 575
Val Lys Val Ile Val Leu Asn Asn Glu Glu Gln Gly Met Val Thr Gln
                580                 585                 590
Trp Gln Asn Leu Phe Tyr Glu Asp Arg Tyr Ala His Thr His Gln Val
                595                 600                 605
Asn Pro Asp Phe Met Lys Leu Ala Glu Ser Met Arg Val Gln Gly Arg
                610                 615                 620
Arg Cys Val Asp Pro Glu Asp Val Val Asp Ser Leu Lys Trp Leu Ile
625                 630                 635                 640
Asn Thr Asp Gly Pro Ala Leu Leu Glu Val Val Thr Asp Lys Lys Val
                645                 650                 655
Pro Val Leu Pro Met Val Pro Ala Gly Ser Ala Leu His Glu Phe Leu
                660                 665                 670
Val Phe Asp Gly Glu Lys Asp Lys Lys Arg Arg Glu Leu Met Arg Glu
                675                 680                 685
Arg Thr Ser Gly Leu His Gly
690                 695
```

GDC-2 GENES CONFERRING HERBICIDE RESISTANCE

CROSS-REFERENCE TO RELATED APPLICATIONS

This application is a continuation-in-part of copending U.S. patent application Ser. No. 10/797,416, filed Mar. 10, 2004, which claims the benefit of U.S. Provisional Application Ser. No. 60/453,149, filed Mar. 10, 2003, each of which is hereby incorporated in its entirety by reference herein.

FIELD OF THE INVENTION

This invention provides novel genes encoding herbicide resistance, which are useful in plant biology, crop breeding, and plant cell culture.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid to 5-enolpyruvyl-3-phosphoshikimic acid. Inhibition of this enzyme (5-enolpyruvylshikimate-3-phosphate synthase; referred to herein as "EPSP synthase") kills plant cells by shutting down the shikimate pathway, thereby inhibiting aromatic acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases may have a high tolerance to glyphosate.

Plant cells resistant to glyphosate toxicity can be produced by transforming plant cells to express glyphosate-resistant EPSP synthases. A mutated EPSP synthase from *Salmonella typhimurium* strain CT7 confers glyphosate resistance in bacterial cells, and confers glyphosate resistance on plant cells (U.S. Pat. Nos. 4,535,060, 4,769,061, and 5,094,945). Thus, there is a precedent for the use of glyphosate-resistant bacterial EPSP synthases to confer glyphosate resistance upon plant cells.

An alternative method to generate target genes resistant to a toxin (such as an herbicide) is to identify and develop enzymes that result in detoxification of the toxin to an inactive or less active form. This can be accomplished by identifying enzymes that encode resistance to the toxin in a toxin-sensitive test organism, such as a bacterium.

Castle et al (WO 02/36782 A2) describe proteins (glyphosate N-acetyltransferases) that are described as modifying glyphosate by acetylation of a secondary amine to yield N-acetylglyphosate.

Barry et al. (U.S. Pat. No. 5,463,175) describes genes encoding an oxidoreductase (GOX), and states that GOX proteins degrade glyphosate by removing the phosphonate residue to yield amino methyl phosphonic acid (AMPA). This suggests that glyphosate resistance can also be conferred, at least partially, by removal of the phosphonate group from glyphosate. However, the resulting compound (AMPA) appears to provide reduced but measurable toxicity upon plant cells. Barry describes the effect of AMPA accumulation on plant cells as resulting in effects including chlorosis of leaves, infertility, stunted growth, and death. Barry (U.S. Pat. No. 6,448,476) describes plant cells expressing an AMPA-N-acetyltransferase (phnO) to detoxify AMPA.

Phophonates, such as glyphosate, can also be degraded by cleavage of C—P bond by a C—P lyase. Wacket et al. (1987) *J. Bacteriol.* 169:710-717) described strains that utilize glyphosate as a sole phosphate source. Kishore et al. (1987) *J. Biol. Chem.* 262:12164-12168 and Shinabarger et al. (1986) *J. Bacteriol.* 168:702-707 describe degradation of glyphosate by C—P Lyase to yield glycine and inorganic phosphate.

While several strategies are available for detoxification of toxins, such as the herbicide glyphosate, as described above, new activities capable of degrading glyphosate are useful. Novel genes and genes conferring glyphosate resistance by novel mechanisms of action would be of additional usefulness. Single genes conferring glyphosate resistance by formation of non-toxic products would be especially useful.

Further, genes conferring resistance to other herbicides, such as the sulfonylureas or imidazolinones, are useful. The sulfonylurea and imidazolinine herbicides are widely used in agriculture because of their efficacy at low use rates against a broad spectrum of weeds, lack of toxicity to mammals, and favorable environmental profile (Saari et al. (1994), p. 83-139 in: *Herbicide Resistance in Plants: Biology and Biochemistry.* S. Powles and J. Holtum eds. Lewis Publishers, Inc., Boca Raton, Fla.). These herbicides act by inhibiting acetohydroxyacid synthase (AHAS, also known as acetolactate synthase) and thereby preventing the biosynthesis of the branched-chain amino acids valine, leucine and isoleucine.

Current methods of herbicide tolerance confer upon a plant tolerance to herbicides with a particular target or mode of action. However, repeated and extensive use of herbicides with a single mode of action can result in the selection of tolerant weed species (Saari et al., supra.). Crop plants which are resistant to more than one class of herbicides (with different modes of action) allow growers flexibility in weed control and are useful in preventing/managing the emergence of resistant weed populations. It would be particularly desirable to generate a plant containing a single trait that conferred tolerance to more than one class of herbicide. Thus, genes encoding resistance to more than one class of herbicide are useful.

Thus, novel genes encoding resistance to herbicides are needed.

SUMMARY OF INVENTION

Compositions and methods for conferring herbicide resistance to plants, plant cells, tissues and seeds are provided. Compositions comprising a coding sequence for a polypeptide that confers resistance or tolerance to glyphosate herbicides are provided. The coding sequences can be used in DNA constructs or expression cassettes for transformation and expression in plants. Compositions also comprise transformed plants, plant cells, tissues, and seeds.

In particular, isolated nucleic acid molecules corresponding to herbicide resistance-conferring nucleic acid sequences are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:3, or a nucleotide sequence set forth in SEQ ID NO:1 or 2, as well as variants and fragments thereof. Nucleotide sequences that are complementary to a nucleotide sequence of the invention, or that hybridize to a sequence of the invention are also encompassed.

DETAILED DESCRIPTION

Figure 1:
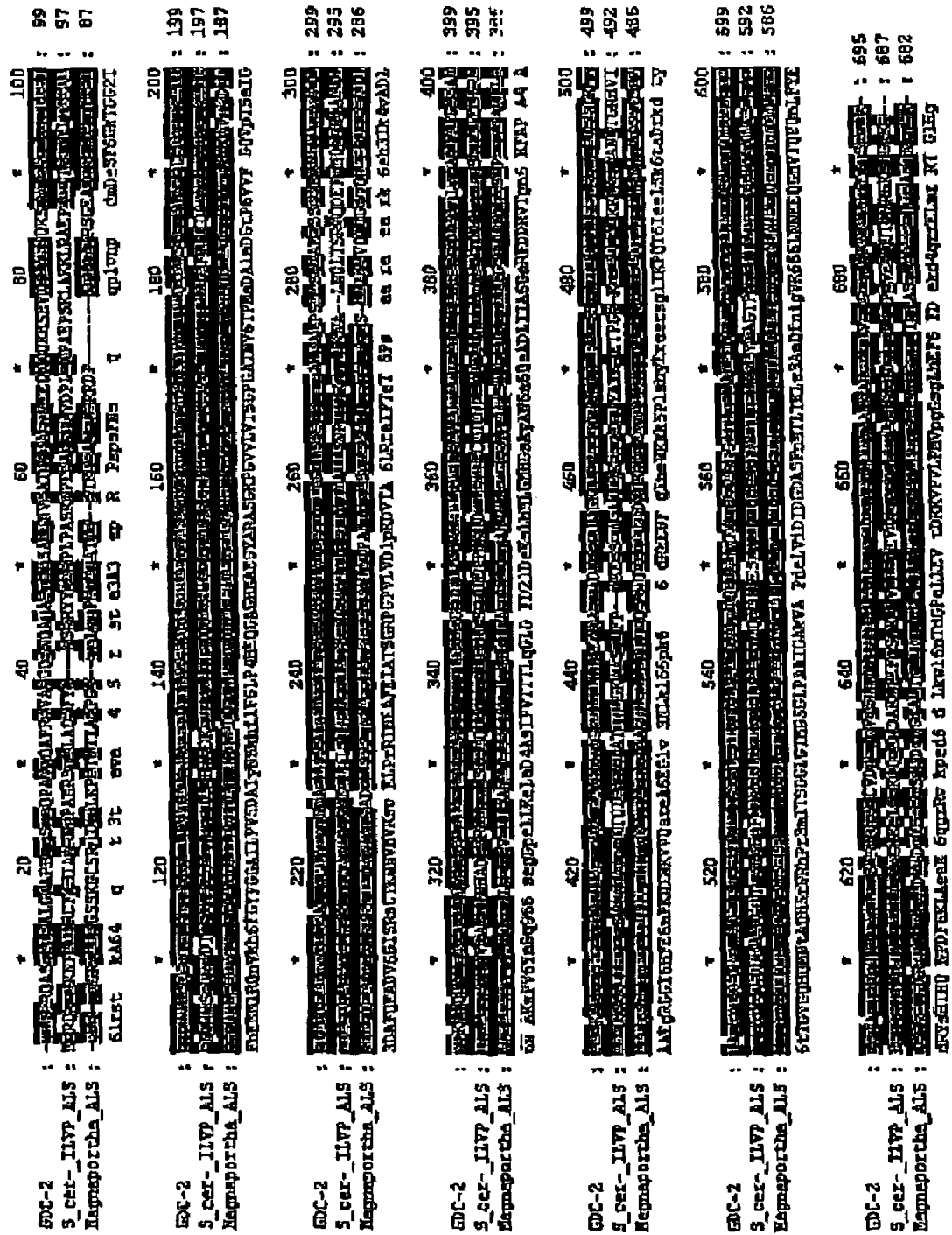
FIG. 1 shows an alignment of GDC-2 protein (SEQ ID NO:3) to acetolactute synthase from *Saccharomyces cerovesiae* (SEQ ID NO:4) and aectolactate synthase from *Magnaporthe grisea* (SEQ ID NO:5). The alignment shows the most highly conserved amino acid residues highlighted in black, and highly conserved amino acid residues highlighted in gray.

The present invention is drawn to compositions and methods for regulating resistance in organisms, particularly in plants or plant cells. The methods involve transforming organisms with nucleotide sequences encoding an herbicide resistance protein of the invention. In particular, the nucleotide sequences of the invention are useful for preparing plants and microorganisms that show increased tolerance to the herbicide glyphosate. Thus, transformed plants, plant cells, plant tissues and seeds are provided. Compositions include nucleic acids and proteins relating to herbicide tolerance in plants as well as transformed plants, plant tissues and seeds. More particularly, nucleotide sequences encoding all or part of the "glyphosate resistance-conferring decarboxylase" gene GDC-2 and the amino acid sequences of the proteins encoded thereby are disclosed. The sequences find use in the construction of expression vectors for subsequent transformation into organisms of interest, as probes for the isolation of other herbicide resistance genes, as selectable markers, and the like.

Definitions

"Glyphosate" includes any herbicidal form of N-phosphonomethylglycine (including any salt thereof) and other forms that result in the production of the glyphosate anion in planta.

"Glyphosate (or herbicide) resistance-conferring decarboxylase" or "GDC" includes a DNA segment that encodes all or part of a glyphosate (or herbicide) resistance protein. This includes DNA segments that are capable of expressing a protein that confers glyphosate (herbicide) resistance to a cell.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer time than cells that do not express the protein.

A "glyphosate resistance protein" includes a protein that confers upon a cell the ability to tolerate a higher concentration of glyphosate than cells that do not express the protein, or to tolerate a certain concentration of glyphosate for a longer time than cells that do not express the protein. By "tolerate" or "tolerance" is intended either to survive, or to carry out essential cellular functions such as protein synthesis and respiration in a manner that is not readily discernable from untreated cells.

By "decarboxylase" is intended a protein, or gene encoding a protein, whose catalytic mechanism can include cleavage and release of a carboxylic acid. This includes enzymes that liberate $CO_2$, such as pyruvate decarboxlyases, acetolactate synthases, and orthinine decarboxylases, as well as enzymes that liberate larger carboxylic acids. "Decarboxylase" includes proteins that utilize thiamine pyrophoshate as a cofactor in enzymatic catalysis. Many such decarbolyases also utilize other cofactors, such as FAD.

By "TPP-binding domain" is intended a region of conserved amino acids present in enzymes that are capable of utilizing TPP as a cofactor.

"Plant tissue" includes all known forms of plants, including undifferentiated tissue (e.g. callus), suspension culture cells, protoplasts, plant cells including leaf cells, root cells, and phloem cells, plant seeds, pollen, propagules, embryos and the like.

"Plant expression cassette" includes DNA constructs that are capable of resulting in the expression of a protein from an open reading frame in a plant cell. Typically these contain a promoter and a coding sequence. Often, such constructs will also contain a 3' untranslated region. Such constructs may contain a 'signal sequence' or 'leader sequence' to facilitate co-translational or post-translational transport of the peptide to certain intracellular structures such as the chloroplast (or other plastid), endoplasmic reticulum, or Golgi apparatus.

"Signal sequence" includes sequences that are known or suspected to result in cotranslational or post-translational peptide transport across the cell membrane. In eukaryotes, this typically involves secretion into the Golgi apparatus, with some resulting glycosylation.

"Leader sequence" includes any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

"Plant transformation vector" includes DNA molecules that are necessary for efficient transformation of a plant cell. Such a molecule may consist of one or more plant expression cassettes, and may be organized into more than one 'vector' DNA molecules. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451).

"Vector" refers to a nucleic acid construct designed for transfer between different host cells. "Expression vector" refers to a vector that has ability to incorporate, integrate and express heterologous DNA sequences or fragments in a foreign cell.

"Transgenic plants" or "transformed plants" or "stably transformed plants or cells or tissues" refers to plants that have incorporated or integrated exogenous or endogenous nucleic acid sequences or DNA fragments or chimeric nucleic acid sequences or fragments.

"Heterologous" generally refers to the nucleic acid sequences that are not endogenous to the cell or part of the native genome in which they are present, and have been added to the cell by infection, transfection, microinjection, electroporation, microprojection, or the like.

"Promoter" refers to a nucleic acid sequence that functions to direct transcription of a downstream coding sequence. The promoter together with other transcriptional and translational regulatory nucleic acid sequences, (also termed as "control sequences") are necessary for the expression of a DNA sequence of interest.

Provided here is a novel isolated gene that confers resistance to an herbicide. Also provided is an amino acid sequence of the GDC-2 protein. The protein resulting from translation of this gene allows cells to function in the presence of concentrations of an herbicide that are otherwise toxic to cells including plant cells and bacterial cells.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated glyphosate resistance-encoding nucleic acid molecule can contain less than about 5 kb, 4 kb, 3 kb, 2 kb, 1 kb, 0.5 kb, or 0.1 kb of nucleotide sequence that naturally flanks the nucleic acid molecule in genomic DNA of the cell from which the nucleic acid is derived. An herbicide resistance protein that is substantially free of cellular material includes preparations of protein having less than about 30%, 20%, 10%, or 5% (by dry weight) of non-herbicide resistance protein (also referred to herein as a "contaminating protein"). Various aspects of the invention are described in further detail in the following subsections.

Isolated Nucleic Acid Molecules, and Variants and Fragments Thereof

One aspect of the invention pertains to isolated nucleic acid molecules comprising nucleotide sequences encoding herbicide resistance proteins and polypeptides or biologically active portions thereof, as well as nucleic acid molecules sufficient for use as hybridization probes to identify herbicide resistance-encoding nucleic acids. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the proteins of the present invention include the sequences set forth in SEQ ID NOS: 1 and 2, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the herbicide resistance protein encoded by these nucleotide sequences is set forth in SEQ ID NO:3. The invention also encompasses nucleic acid molecules comprising nucleotide sequences encoding partial-length herbicide resistance proteins, and complements thereof.

Nucleic acid molecules that are fragments of these herbicide resistance-encoding nucleotide sequences are also encompassed by the present invention. By "fragment" is intended a portion of the nucleotide sequence encoding an herbicide resistance protein. A fragment of a nucleotide sequence may encode a biologically active portion of an herbicide resistance protein, or it may be a fragment that can be used as a hybridization probe or PCR primer using methods disclosed below. Nucleic acid molecules that are fragments of an herbicide resistance nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600 nucleotides, or up to the number of nucleotides present in a full-length herbicide resistance-encoding nucleotide sequence disclosed herein (for example, 2606 nucleotides for SEQ ID NO:1) depending upon the intended use.

Fragments of the nucleotide sequences of the present invention generally will encode protein fragments that retain the biological activity of the full-length glyphosate resistance protein; i.e., herbicide-resistance activity. By "retains herbicide resistance activity" is intended that the fragment will have at least about 30%, preferably at least about 50%, more preferably at least about 70%, even more preferably at least about 80% of the herbicide resistance activity of the full-length glyphosate resistance protein disclosed herein as SEQ ID NO:3. Methods for measuring herbicide resistance activity are well known in the art. See, for example, U.S. Pat. Nos. 4,535,060, and 5,188,642, each of which are herein incorporated by reference in their entirety.

A fragment of an herbicide resistance-encoding nucleotide sequence that encodes a biologically active portion of a protein of the invention will encode at least about 15, 25, 30, 50, 75, 100, 125, 150, 175, 200, 250, 300, 350, 400, 450, 500, 550, 600, 650 contiguous amino acids, or up to the total number of amino acids present in a full-length herbicide resistance protein of the invention (for example, 696 amino acids for the protein of the invention).

Preferred herbicide resistance proteins of the present invention are encoded by a nucleotide sequence sufficiently identical to the nucleotide sequence of SEQ ID NO:1 or 2. The term "sufficiently identical" is intended an amino acid or nucleotide sequence that has at least about 60% or 65% sequence identity, preferably about 70% or 75% sequence identity, more preferably about 80% or 85% sequence identity, most preferably about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to GDC-like nucleic acid molecules of the invention. BLAST protein searches can be performed with the BLASTX program, score=50, wordlength=3, to obtain amino acid sequences homologous to herbicide resistance protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov. Another non-limiting example of a mathematical algorithm utilized for the comparison of sequences is the ClustalW algorithm (Higgins et al.(1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the vector NTi Program Suite (Informax, Inc). After alignment of amino acid sequences with ClustalW, the percent amino acid identity can be assessed. A non-limiting example of a software program useful for analysis of ClustalW alignments is GeneDoc™. Genedoc™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA). When utilizing the ALIGN program for comparing amino acid sequences, a PAM120 weight residue table, a gap length penalty of 12, and a gap penalty of 4 can be used.

A preferred program is GAP version 10, which used the algorithm of Needleman and Wunsch (1970) supra. GAP Version 10 may be used with the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 Scoring Matrix. Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The invention also encompasses variant nucleic acid molecules. "Variants" of the herbicide resistance-encoding nucleotide sequences include those sequences that encode the herbicide resistance protein disclosed herein but that differ conservatively because of the degeneracy of the genetic code, as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the herbicide resistance proteins disclosed in the present invention as discussed below. Variant proteins encompassed by the present invention are biologically active, that is they retain the desired biological activity of the native protein, that is, herbicide resistance activity. By "retains herbicide resistance activity" is intended that the variant will have at least about 30%, preferably at least about 50%, more preferably at least about 70%, even more preferably at least about 80% of the herbicide resistance activity of the native protein. Methods for measuring herbicide resistance activity are well known in the art. See, for example, U.S. Pat. Nos. 4,535,060, and 5,188,642, each of which are herein incorporated by reference in their entirety.

The skilled artisan will further appreciate that changes can be introduced by mutation into the nucleotide sequences of the invention thereby leading to changes in the amino acid sequence of the encoded herbicide resistance proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, preferably nonessential amino acid residues. A "nonessential" amino acid residue is a residue that can be altered from the wild-type sequence of an herbicide resistance protein without altering the biological activity, Whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function, In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in the alignment of FIG. 1. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer herbicide resistance activity to identify mutants that retain activity. Following mutagenesis, the encoded protein can be expressed recombinantly, and the activity of the protein can be determined using standard assay techniques.

Using methods such as PCR, hybridization, and the like corresponding herbicide resistance sequences can be identified, such sequences having substantial identity to the sequences of the invention. See, for example, Sambrook J., and Russell, D. W. (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the herbicide resistance nucleotide sequence can be used to screen cDNA or genomic libraries. Methods for construction of such cDNA and genomic libraries are generally known in the art and are disclosed in Sambrook and Russell, 2001. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known herbicide resistance-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, preferably about 25, more preferably at least about 50, 75, 100, 125, 150, 175, 200, 250, 300, 350, or 400 consecutive nucleotides of herbicide resistance-encoding nucleotide sequence of the invention or a fragment or variant thereof. Preparation of probes for hybridization is generally known in the art and is disclosed in Sambrook and Russell, 2001, and Sambrook et al. (1989) *Molecular Cloning: A Laboratory Manual* (2d ed., Cold Spring Harbor Laboratory Press, Plainview, N.Y.), both of which are herein incorporated by reference.

For example, an entire herbicide resistance sequence disclosed herein, or one or more portions thereof, may be used as a probe capable of specifically hybridizing to corresponding herbicide resistance sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify corresponding herbicide resistance sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCi, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Isolated Proteins and Variants and Fragments Thereof

Herbicide resistance proteins are also encompassed within the present invention. By "herbicide resistance protein" is intended a protein having the amino acid sequence set forth in SEQ ID NO3. Fragments, biologically active portions, and variants thereof are also provided, and may be used to practice the methods of the present invention.

"Fragments" or "biologically active portions" include polypeptide fragments comprising a portion of an amino acid sequence encoding an herbicide resistance protein as set forth in SEQ ID NO:3 and that retains herbicide resistance activity. A biologically active portion of an herbicide resistance protein can be a polypeptide that is, for example, 10, 25, 50, 100 or more amino acids in length. Such biologically active portions can be prepared by recombinant techniques and evaluated for herbicide resistance activity. Methods for measuring herbicide resistance activity are well known in the art. See, for example, U.S. Pat. Nos. 4,535,060, and 5,188,642, each of which are herein incorporated by reference in their entirety. As used here, a fragment comprises at least 8 contiguous amino acids of SEQ ID NO:3. The invention encompasses other fragments, however, such as any fragment in the protein greater than about 10, 20, 30, 50, 100, 150, 200, 250, 300, 350, 400, 450, 500, 550, or 600 amino acids.

By "variants" is intended proteins or polypeptides having an amino acid sequence that is at least about 60%, 65%, preferably about 70%, 75%, more preferably 80%, 85%, most preferably 90%, 91%, 92%, 93%, 94%, 95%, 96%, 97%, 98% or 99% identical to the amino acid sequence of SEQ ID NO:3. Variants also include polypeptides encoded by a nucleic acid molecule that hybridizes to the nucleic acid molecule of SEQ ID NO:1 or 2, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining herbicide resistance activity. Methods for measuring herbicide resistance activity are well known in the art. See, for example, U.S. Pat. Nos. 4,535,060, and 5,188,642, each of which are herein incorporated by reference in their entirety.

Altered or Improved Variants

It is recognized that DNA sequence of GDC-2 may be altered by various methods, and that these alterations may result in DNA sequences encoding proteins with amino acid sequences different that that encoded by GDC-2. This protein may be altered in various ways including amino acid substitutions, deletions, truncations, and insertions. Methods for such manipulations are generally known in the art. For example, amino acid sequence variants of the GDC-2 protein can be prepared by mutations in the DNA. This may also be accomplished by one of several forms of mutagenesis and/or in directed evolution. In some aspects, the changes encoded in the amino acid sequence will not substantially affecting function of the protein. Such variants will possess the desired herbicide resistance activity. However, it is understood that the ability of GDC-2 to confer herbicide resistance may be improved by one use of such techniques upon the compositions of this invention. For example, one may express GDC-2 in host cells that are have exhibit high rates of base misincorporation during DNA replication, such as XL-1 Red (Stratagene). After propagation in such strains, one can isolate the GDC-2 DNA (for example by preparing plasmid DNA, or by amplifying by PCR and cloning the resulting PCR fragment into a vector), culture the GDC-2 mutations in a non-mutagenic strain, and identify mutated GDC-2 genes with improved resistance to an herbicide such as glyphosate, for example by growing cells in increasing concentrations of glyphosate and testing for clones that confer ability to tolerate increased concentrations of glyphosate.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different herbicide resistance protein coding regions can be used to create a new herbicide resistance protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the herbicide resistance gene of the invention and other known herbicide resistance genes to obtain a new gene coding for a protein with an improved property of interest, such as an increased glyphosate resistance activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Transformation of Bacterial or Plant Cells

In one aspect of the invention, the GDC-2 gene is useful as a marker to assess transformation of bacterial or plant cells. Transformation of bacterial cells is accomplished by one of several techniques known in the art, not limited to electroporation, or chemical transformation (See for example Ausubel (ed.), Current Protocols in Molecular Biology, John Wiley and Sons, Inc. (1994)). Markers conferring resistance to toxic substances are useful in identifying transformed cells (having taken up and expressed the test DNA) from non-transformed cells (those not containing or not expressing the test DNA). By engineering GDC-2 to be (1) expressed from a bacterial promoter known to stimulate transcription in the organism to be tested, (2) properly translated to generate an intact GDC-2 peptide, and (3) placing the cells in an otherwise toxic concentration of herbicide, one can identify cells that have been transformed with DNA by virtue of their resistance to herbicide.

Transformation of plant cells can be accomplished in similar fashion. First, one engineers the GDC-2 gene in a way that allows its expression in plant cells. The herbicide resistance sequences of the invention may be provided in expression cassettes for expression in the plant of interest. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes. The organization of such constructs is well known in the art.

Such an expression cassette is provided with a plurality of restriction sites for insertion of the herbicide resistance sequence to be under the transcriptional regulation of the regulatory regions. The expression cassette will include in the 5'-3' direction of transcription, a transcriptional and translational initiation region (i.e., a promoter), a DNA sequence of the invention, and a transcriptional and translational termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably-linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens,* such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing host-preferred genes. See, for example, U.S. Pat. Nos. 6,320,100; 6,075,185; 5,380,831; and 5,436,391, U.S. Published application Nos. 20040005600 and 20010003849, and Murray et al. (1989) *Nucleic Acids Res.* 17:477-498, herein incorporated by reference.

In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression. In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this 'plant expression cassette' will be inserted into a 'plant transformation vector'. This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as 'binary vectors'. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a 'gene of interest' (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium,* and transfer of DNA by cleavage at border sequences and vir-mediated DNA transfer, as in understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethelene glycol, etc. Many types of vectors can be used to transform plant cells for achieving herbicide resistance.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene and in one case "glyphosate") to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoot or plantlet. The transgenic plantlet then grow into mature plant and produce fertile seeds (e.g. Hiei et al. (1994) The Plant Journal 6:271-282; Ishida et al. (1996) Nature Biotechnology 14:745-750). Explants are typically transferred to a fresh supply of the same medium and cultured routinely. A general description of the techniques and methods for generating transgenic plants are found in Ayres and Park (1994) Critical Reviews in Plant Science 13:219-239 and Bommineni and Jauhar (1997) Maydica 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Generation of transgenic plants may be performed by one of several methods, including but not limited to introduction of heterologous DNA by *Agrobacterium* into plant cells (*Agrobacterium*-mediated transformation), bombardment of plant cells with heterologous foreign DNA adhered to particles including aerosol beam transformation (U.S. Published application No. 20010026941; U.S. Pat. No. 4,945,050; International Publication No. WO 91/00915; U.S. Published application No. 2002015066), and various other non-particle direct-mediated methods (e.g. Hiei et al. (1994) The Plant Journal 6:271-282; Ishida et al. (1996) Nature Biotechnology 14:745-750; Ayres and Park (1994) Critical Reviews in Plant Science 13:219-239; Bommineni and Jauhar (1997) Maydica 42:107-120) to transfer DNA.

Following integration of heterologous foreign DNA into plant cells, one then applies a maximum threshold level of herbicide in the medium to kill the untransformed cells and separate and proliferate the putatively transformed cells that survive from this selection treatment by transferring regularly to a fresh medium. By continuous passage and challenge with herbicide, one identifies and proliferates the cells that are transformed with the plasmid vector. Then molecular and biochemical methods will be used for confirming the presence of the integrated heterologous gene of interest in the genome of transgenic plant.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR Analysis: PCR analysis is a rapid method to screen transformed cells, tissue or shoots for the presence of incorporated gene at the earlier stage before transplanting into the soil (Sambrook and Russell, 2001). PCR is carried out using oligonucleotide primers specific to the gene of interest or Agrobacterium vector background, etc.

Southern Analysis: Plant transformation is confirmed by Southern blot analysis of genomic DNA (Sambrook and Russell, 2001). In general, total DNA is extracted from the transformant, digested with appropriate restriction enzymes, fractionated in an agarose gel and transferred to a nitrocellulose or nylon membrane. The membrane or "blot" then is probed with, for example, radiolabeled $^{32}$P target DNA fragment to confirm the integration of introduced gene in the plant genome according to standard techniques (Sambrook and Russell, 2001. *Molecular Cloning: A Laboratory Manual.* Cold Spring Harbor Laboratory Press, Cold Spring Harbor, N.Y.).

Northern Analysis: RNA is isolated from specific tissues of transformant, fractionated in a formaldehyde agarose gel, blotted onto a nylon filter according to standard procedures that are routinely used in the art (Sambrook, J., and Russell, D. W. 2001. *Molecular Cloning: A Laboratory Manual,* Cold Spring Harbor Laboratory Press, Cold Spring Harbor, N.Y.). Expression of RNA encoded by the GDC-2 is then tested by hybridizing the filter to a radioactive probe derived from a GDC, by methods known in the art (Sambrook and Russell, 2001)

Western blot and Biochemical assays: Western blot and biochemical assays and the like may be carried out on the transgenic plants to determine the presence of protein encoded by the herbicide resistance gene by standard procedures (Sambrook, J., and Russell, D. W. 2001. *Molecular Cloning: A Laboratory Manual,* Cold Spring Harbor Laboratory Press, Cold Spring Harbor, N.Y.) using antibodies that bind to one or more epitopes present on the herbicide resistance protein.

Transgenic Plants

In another aspect of the invention, one may generate transgenic plants expressing GDC-2 that are more resistant to high concentrations of herbicide than non-transformed plants. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing GDC-2 may be isolated by common methods described in the art, for example by transformation of callus, selection of transformed callus, and regeneration of fertile plants from such transgenic callus. In such process, GDC-2 may be used as selectable marker. Alternatively, one may use any gene as a selectable marker so long as its expression in plant cells confers ability to identify or select for transformed cells. Genes known to function effectively as selectable markers in plant transformation are well known in the art.

Resistance to Sulfonylurea (SLT) and/or Imidazolinone Herbicides

Sulfonylurea and imidizolinone herbicides act by inhibiting acetohydroxyacid synthase and thus preventing the biosynthesis of the branched-chain amino acids. Some naturally occurring or mutated forms of AHAS are highly resistant to inhibition by these herbicides. Introduction of these resistant AHAS genes into crop plants by breeding, mutation/selection, or recombinant DNA methods can confer herbicide resistance to the crop. GDC-2 has high homology to the sulfonylurea resistant AHAS gene from *Magnaporthe grisea* described by Sweigard et al. (1997) *Fungal Genet. Newsl.* 44:52-53) and thus GDC-2 may be naturally resistant to sulfonylureas and imidizolinones, and confer that resistance to transformed plants. Furthermore, the amino acid changes which result in resistance for plant and bacterial AHAS enzymes are well known in the art (e.g., Bemasconi et al. (1995) *J. Biol. Chem.* 270:17381-17385; Lee and Duggleby (2000) *Biochem. J.* 350:69-73). If necessary, analogous changes may be made in the GDC-2 gene to improve its resistance to herbicides using well-known techniques.

The following examples are offered by way of illustration and not by way of limitation.

EXPERIMENTAL

Example 1

Isolation of.ATX6837 (from 50 mM Glyphosate Stock)

Strain ATX6837 was identified as a contaminant growing in a laboratory stock of 50 mM glyphosate. ATX6837 was isolated from this stock by methods known in the art.

Example 2

Construction of cDNA Library from Strain ATX6837

ATX6837 was grown in (liquid media L+phosphorous) containing 5 mM glyphosate, and total RNA was isolated using Trizol reagent (Invitrogen). poly(A)+ mRNA was isolated from total RNA using Poly(A) Purist mRNA Purification kit (Ambion). cDNA was synthesized from polyA+ mRNA using ZAP CDNA Synthesis kit from Stratagene, and cloned into the lambda Zap II expression vector (Stratagene).

Example 3

In vivo Excision of cDNA Clones

The ATX6837 cDNA library was excised in bulk as per manufacturers protocol (Stratagene), and transfected into the SOLR strain of *E. coli* (Stratagene), and plated directly on M9 minimal media plates containing thiamine, proline, ampicillin and 7 mM glyphosate and incubated at 37° C. (M9 media contains 30 g $Na_2HPO_4$, 15 g $KH_2PO_4$, 5 g $NH_4Cl$, 2.5 g NaCl, and 15 mg $CaCl_2$).

Example 4

Identification of cDNA Clones Conferring Glyphosate Resistance in *E. coli*

Following 2 days growth, approximately 520 of $2.5 \times 10^6$ colony forming units plated (0.02%) had grown in the presence of 7 mM glyphosate. These colonies were transferred onto M9 plates containing 10 mM glyphosate for further selection. Twenty six clones were identified as having the ability to grow on M9 plates containing 10 mM glyphosate, and these were chosen for further studies. Plasmid DNA from the 26 positive clones was isolated and transformed into the alternate host strain XL-1 Blue MRF' (Stratagene) and plasmid DNA was prepared for sequencing. Clones were replated on M9 plates containing 10 mM glyphosate, and clone E-F9 was found to grow on these plates.

We determined the DNA sequence of 26 clones conferring glyphosate resistance at both 7 mM and 10 mM glyphosate levels. Clone E-F9 was determined to contain a large open reading frame. Analysis of the large open reading frame, as well as comparison of the predicted amino acid sequence with protein databases suggest that the open reading frame in clone E-F9 represents a full length cDNA. We have designated this open reading frame GDC-2. The sequence of the GDC-2 open reading frame as contained in clone E-F9 is provided in SEQ ID NO:1 respectively.

Example 5

GDC-2 Does Not Complement an aroA Mutation in *E. coli*

The *E. coli* aroA gene codes for EPSP synthase, the target enzyme for glyphosate. EPSP synthase catalyzes the sixth step in the biosynthesis of aromatic amino acids in microbes and plants. aroA mutants that lack an EPSP synthase do not grow on minimal media that lacks aromatic amino acids (Pittard and Wallace (1966) *J. Bacteriol.* 91:1494-508), but can grow in rich media, such as LB. However, genes encoding EPSPS activity can restore the ability to grow on glyphosate upon aroA mutant *E. coli* strains. Thus, a test for genetic complementation of an aroA mutant is a highly sensitive method to test if a gene is capable of functioning as an EPSPS in *E. coli*. Such tests for gene function by genetic complementation are known in the art.

A deletion of the aroA gene was created in *E. coli* XL-1 MRF' (Stratagene) by PCR/recombination methods known in the art and outlined by Datsenko and Wanner, (2000) *Proc. Natl. Acad. Sci. USA* 97:6640-6645. This system is based on the Red system that allows for chromosomal disruptions of targeted sequences. A large portion (1067 nt of the 1283 nt) of the aroA coding region was disrupted by the engineered deletion. The presence of the deletion was confirmed by PCR with several sets of oligonucleotides, and by the appearance of an aroA phenotype in the strain, referred to herein as 'ΔaroA'. ΔaroA grows on LB media (which contains all amino acids) and grows on M63 media supplemented with phenylalanine, tryptophan, and tyrosine, but does not grow on M63 minimal media (which lacks aromatic amino acids). These results indicate that ΔaroA exhibits an aroA phenotype.

The ability of an EPSPS to complement the mutant phenotype of ΔaroA was confirmed. Clone pAX482, an *E. coli* expression vector containing the wild-type *E. coli* aroA gene, was transformed into ΔaroA, and transformed cells were selected. These cells (containing a functional aroA gene residing on a plasmid) were then plated on LB media, M63, and M63 with amino acid supplements. Where the ΔaroA mutant strain grew only on LB and M63 supplemented with aromatic amino acids, ΔaroA cells containing the functional aroA gene on a plasmid grew on all three media types. In order to determine whether or not GDC-2 could confer complementation, plasmid pAX473, the expression vector containing GDC-2 was transformed into ΔaroA and plated on the same three types of media. Cells transformed with pAX473 were able to grow on M63 media supplemented with phenylalanine, tryptophan, and tyrosine and LB media but they were not able to grow on M63 alone. Thus, GDC-2 was not capable of complementing the aroA mutation, and thus GDC-2 is not an EPSP synthase.

Example 6

GDC-2 is a Homologue of Acetolactate Synthase

The predicted amino acid sequence of GDC-2 was compared to the non-redundant database of sequences maintained by the National Center for Biotechnology Information (NCBI), using the BLAST2 algorithm (Altschul et al. (1990) *J. Mol. Biol.* 215:403-410; Altschul et al. (1997) *Nucleic Acids Res.* 25:3389-3402; Gish and States (1993) *Nature Genet.* 3:266-272). The results of BLAST searches identified homology between the predicted GDC-2 open reading frame (SEQ ID NO:3) and several known proteins. The highest scoring amino acid sequences from this search were aligned with GDC-2 using ClustalW algorithm (Higgins et al. (1994) *Nucleic Acids Res.* 22:4673-4680) [as incorporated into the program ALIGNX module of the Vector NTi Program Suite, Informax, Inc.]. After alignment with ClustalW, the percent amino acid identity was assessed. The percent amino acid identity of GDC-2 with members of these protein classes is shown in Table 1.

TABLE 1

Percent identity of GDC-2 to related proteins from various fungi and bacteria

| Organism | Gene Product | % amino acid identity |
| --- | --- | --- |
| *Magnaportha grisae* | Acetolactate synthase | 77% |
| *Saccharomyces cerevisiae* | Acetolactate synthase | 58% |

Further analysis of GDC-2 sequence shows that GDC-2 contains conserved domains characteristic of proteins that utilize Thiamine Pyrophosphale (TPP) as a cofactor. These domains are collectively and singly referred to as a "TPP binding domain". Analysis of GDC-2 sequence shows that amino acids 95-255 of SEQ ID NO:3 constitute an N-terminal domain of TPP-binding domain, amino acids 293-453 of SEQ ID NO:3 constitute a central domain of TPP-binding domain, and amino acids 476-650 of SEQ ID NO:3 constitute a C-terminal domain of TPP-binding domain. It is understood that these amino acid coordinates are only approximations of the location of such domains as judged by homology with known TPP-binding proteins, and are not limiting to the invention. An alignment of GDC-2 with other known TPP-binding proteins is shown in FIG. 1.

Example 7

Measurement of Glyphosate Modification Activity

Glyphosate activity is measured using isotopically labelled glyphosate molecules. In one aspect of the method, a mixture of isotopically labelled and non-labelled molecules is utilized. Alternatively, a mixture of isotopically labelled glyphosate molecules is utilized, for example a 50:50 mixture of glyphosate-(glycine-2-$^{14}$C) and glyphosate-(phosphonomethyl-$^{14}$C). The glyphosate mixture is incubated in a reaction vessel, such as a test tube or microtiter plate, with a buffer, such as 50 mM Tris, pH 8, a quantity of TPP, such as 1 mM TPP, and a quantity of test enzyme sample. The test enzyme sample can be comprised of a pure enzyme, a partially pure enzyme, a crude cell lysate (such as a lysate of an *E. coli* cell), or a crude culture supernatant. After a sufficient incubation, for example 10 minutes, an aliqout of the reaction mix is removed and analyzed to detect cleavage of glyphosate by the enzyme. This method of analysis can include for example HPLC chromatography and measurement of the retention time of the sample vs $C^{14}$ glyphosate and other standards. Alternatively, this method of analysis can include thin layer chromatography (TLC).

Example 8

Engineering GDC-2 for Expression in *E. coli*

An *E. coli* strain expressing GDC-2 was engineered into a customized expression vector, pAX481. pAX481 contains the pBR322 origin of replication, a chloramphenicol acetyl transferase gene (for selection and maintenance of the plasmid), the lacI gene, the Ptac promoter and the rrnB transcriptional terminator. The GDC-2 open reading frame was amplified by PCR, using a high fidelity DNA polymerase, as known in the art. The oligonucleotides for PCR amplification of GDC-2 were designed to place the ATG start site of the genes at the proper distance from the ribosome binding site of pAX481.

The GDC-2 PCR product was cloned into the expression vector pAX481 and transformed into *E. coli* XL1 Blue MRF' to yield the plasmid pAX473. GDC-2 positive clones were identified by standard methods known in the art. The sequence of pAX472 and pAX473 were confirmed by DNA sequence analysis as known in the art.

Example 9

Purification of GDC-2 Expressed as a 6× His-tagged Protein in *E. coli*

The GDC-2 coding region (2,088 nucleotides) was amplified by PCR using ProofStart™ DNA polymerase (Qiagen). Oligonucleotides used to prime PCR were designed to introduce restriction enzyme recognition sites near the 5' and 3' ends of the resulting PCR product. The resulting PCR product was digested with BamH I and Hind III. BamH I cleaved the PCR product at the 5' end, and Sal I cleaved the PCR product at the 3' end. The digested product was cloned into the 6× His-tag expression vector pQE-30 (Qiagen), prepared by digestion with BamH I and Hind III. The resulting clone, pAX624, contained GDC-2 in the same translational reading frame as, and immediately C-terminal to, the 6× His tag of pQE-30. General strategies for generating such clones, and for expressing proteins containing 6× His-tag are well known in the art.

The ability of this clone to confer glyphosate resistance was confirmed by plating cells of pAX624 onto M63 media containing 5 mM glyphosate. pAX624 containing cells gave rise to colonies, where cells containing the vector alone gave no colonies.

GDC-2 protein from pAX624-containing cells was isolated by expression of GDC-2-6× His-tagged protein in *E.*

*coli*, and the resulting protein purified using Ni-NTA Superflow Resin (Qiagen) as per manufacturer's instructions.

Example 10

Assay of GDC-2 Acetolactate Synthase Activity

Acetolactate synthases are decarboxylating enzymes that condense two pyruvate molecules to form acetolactate with the release of a $CO_2$ moiety from one of the pyruvate substrates. In the detection of the enzymatic reaction described by Pang and Duggleby (Pang and Duggleby (1999) *Biochemistry* 18:5222-5231), the product acetolactate is converted to acetoin by incubation with 1% $H_2SO_4$ for 15 minutes at 60° C. followed by neutralization with KOH. The acetoin is then detected as described by Westerfeld (Westerfeld (1945) *J. Biol. Chem.* 161:495-502), using 0.15% creatine and 1.5% alpha-naphthol (dissolved in 2.5 N NaOH). The red colored reaction product is quantified by absorbance at 525 nm.

Samples containing either 5 μg or 10 μg of GDC-2 were incubated in 50 mM pyruvate, 1 mM thymine pyrophosphate, 10 mM $MgCl_2$, 0.01 mM Flavin adenine dinucleotide (FAD), 100 mM potassium phosphate buffer pH 7.0 (total reaction volume of 50 μl) for 2 hours at 37° C. The reaction was stopped by the addition of 1 μl of 50% sulfuric acid ($H_2SO_4$) and incubated at 60° C. for 15 minutes. The reaction was neutralized by the addition of 30 μl of 1 N KOH followed by the addition of 10 μl of 1.5% creatine and 10 μl of 15% alpha-napthol dissolved in 2.5 N NaOH. The red colored reaction product was quantified by absorbance at 525 nm.

TABLE 3

Acetolactate synthase activity

| Amount GDC-2 (μg) | Absorbance 525 nm) |
|---|---|
| 0 μg (control) | 0.0 |
| 5 μg | 1.99 |
| 10 μg | 3.13 |

Example 11

Engineering GDC-2 for Plant Transformation

The GDC-2 open reading frame (ORF) was amplified by polymerase chain reactions from a full-length cDNA template. Hind III restriction sites were added to each end of the ORF during PCR. Additionally, the nucleotide sequence ACC was added immediately 5' to the start codon of the gene to increase translational efficiency (Kozak (1987) 15:8125-8148; Joshi (1987) *Nucleic Acids Research* 15:6643-6653). The PCR product was cloned and sequenced, using techniques well known in the art, to ensure that no mutations were introduced during PCR.

The plasmid containing the GDC-2 PCR product was digested with Hind III and the fragment containing the intact ORF was isolated. This fragment was cloned into the Hind III site of plasmid pAX200, a plant expression vector containing the rice actin promoter (McElroy et al. (1991) *Molec. Gen. Genet.* 231:150-160) and the PinII terminator (An et al. (1989) *The Plant Cell* 1:115-122). The promoter-gene-terminator fragment from this intermediate plasmid was subcloned plasmid pSB11 (Japan Tobacco, Inc.) to form the plasmid pAX811. PAX811 is organized such that the 3.91 kb DNA fragment containing the promoter—GDC-2—terminator construct may be excised from pAX811 by double digestion with Kpn I and Pme I and used for transformation into plants by aerosol beam injection. The structure of pAX811 was verified by restriction digests and gel electrophoresis and by sequencing across the various cloning junctions.

Plasmid pAX810 was mobilized into *Agrobacterium tumifaciens* strain LBA4404 which also harbored the plasmid pSB1 (Japan Tobacco, Inc.), using triparental mating procedures well known in the art, and plating on media containing spectinomycin. Plasmid pAX811 carries spectinomycin resistance but is a narrow host range plasmid and cannot replicate in *Agrobacterium*. Spectinomycin resistant colonies arise when pAX811 integrates into the broad host range plasmid pSB1 through homologous recombination. The cointegrate product of pSB1 and pAX811 was named pAX205 and was verified by Southern hybridization (data not shown). The *Agrobacterium* strain harboring pAX205 was used to transform maize by the PureIntro method (Japan Tobacco).

Example 12

Transformation of GDC-2 into Plant Cells

Maize ears are collected 8-12 days after pollination. Embryos are isolated from the ears, and those embryos 0.8-1.5 mm in size are used for transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casaminoacids; 50 g/L sucrose; 1 mL/L (of 1 mg/mL Stock) 2,4-D). However, media and salts other than DN62A5S are suitable and are known in the art. Embryos are incubated overnight at 25° C. in the dark.

The resulting explants are transferred to mesh squares (30-40 per plate), transferred onto osmotic media for 30-45 minutes, then transferred to a beaming plate (see, for example, PCT Publication No. WO/0138514 and U.S. Pat. No. 5,240, 842).

DNA constructs designed to express GDC-2 in plant cells are accelerated into plant tissue using an aerosol beam accelerator, using conditions essentially as described in PCT Publication No. WO/0138514. After beaming, embryos are incubated for 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| DN62A5S Media | | |
|---|---|---|
| Components | per liter | Source |
| Chu'S N6 Basal Salt Mixture (Prod. No. C 416) | 3.98 g/L | Phytotechnology Labs |
| Chu's N6 Vitamin Solution (Prod. No. C 149) | 1 mL/L (of 1000× Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casaminoacids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH to 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

Example 13

Transformation of GDC-2 into Plant Cells by Agrobacterium-Mediated Transformation Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an Agrobacterium strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule selected from the group consisting of:
   a) a nucleic acid molecule comprising the nucleotide sequence of SEQ ID NO: 1 or 2, or a complement thereof
   b) a nucleic acid molecule which encodes a polypeptide comprising the amino acid sequence of SEQ ID NO:3; and
   c) a complement of any of a)-b).

2. The isolated nucleic acid molecule of claim 1, wherein said nucleotide sequence is a synthetic sequence that has been designed for expression in a plant.

3. The nucleic acid molecule of claim 2, wherein said synthetic sequence has an increased GC content relative to the GC content of SEQ ID NO:1 or 2.

4. A vector comprising the nucleic acid molecule of claim 1.

5. The vector of claim 4, further comprising a nucleic acid molecule encoding a heterologous polypeptide.

6. A host cell that contains the vector of claim 4.

7. The host cell of claim 6 that is a bacterial host cell.

8. The host cell of claim 6 that is a plant cell.

9. A transgenic plant comprising the host cell of claim 8.

10. The plant of claim 9, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

11. A transgenic seed comprising the nucleic acid molecule of claim 1.

12. A method for producing a polypeptide with herbicide resistance activity, comprising culturing the host cell of claim 6 under conditions in which a nucleic acid molecule encoding the polypeptide is expressed, said polypeptide being selected from the group consisting of:

a) a polypeptide comprising the amino acid sequence of SEQ ID NO:3; and b) a polypeptide encoded by the nucleic acid sequence of SEQ ID NO:2.

13. A method for conferring resistance to an herbicide in a plant, said method comprising transforming said plant with a DNA construct, said construct comprising a promoter that drives expression in a plant cell operably linked with a nucleotide sequence encoding SEQ ID NO:3, and regenerating a transformed plant, wherein said nucleotide sequence encodes a polypeptide that has herbicide resistance activity.

14. The method of claim 13, wherein said herbicide is a glyphosate.

15. A plant having stably incorporated into its genome a DNA construct comprising a nucleotide sequence that encodes a protein having herbicide resistance activity, wherein said nucleotide sequence is selected from the group consisting of:

a) the nucleotide sequence of SEQ ID NO: 1 or 2; and b) a nucleotide sequence encoding a polypeptide comprising the amino acid sequence of SEQ ID NO:3;

wherein said nucleotide sequence is operably linked to a promoter that drives expression of a coding sequence in a plant cell.

16. A plant cell having stably incorporated into its genome a DNA construct comprising a nucleotide sequence that encodes a protein having herbicide resistance activity, wherein said nucleotide sequence is selected from the group consisting of:

a) the nucleotide sequence of SEQ ID NO:1 or 2; and b) a nucleotide sequence encoding a polypeptide comprising the amino acid sequence of SEQ ID NO:3;

wherein said nucleotide sequence is operably linked to a promoter that drives expression of a coding sequence in a plant cell.

17. A method for conferring resistance to sulfonylurea herbicides in a plant, said method comprising transforming said plant with a DNA construct, said construct comprising a promoter that drives expression in a plant cell operably linked with a nucleotide sequence encoding SEQ ID NO:3, wherein said nucleotide sequence encodes a polypeptide having herbicide resistance activity, and regenerating a transformed plant.

* * * * *

UNITED STATES PATENT AND TRADEMARK OFFICE
CERTIFICATE OF CORRECTION

PATENT NO. : 7,538,262 B2
APPLICATION NO. : 11/185560
DATED : May 26, 2009
INVENTOR(S) : Hammer et al.

It is certified that error appears in the above-identified patent and that said Letters Patent is hereby corrected as shown below:

Column 3,
Line 8, "acetolactute" should read --acetolactate--;
Lines 8 and 9, "cerovesiae" should read --cerevesiae--;
Line 9, "aectolactate" should read --acetolactate--;
Line 61, "discemable" should read --discernable--.

Column 17,
Line 3, "(SLT)" should read --(SU)--;
Line 19, "Bemasconi" should read --Bernasconi--.

Column 19,
Line 42, "Pyrophosphale" should read --Pyrophosphate--.

Signed and Sealed this

Sixteenth Day of February, 2010

David J. Kappos
*Director of the United States Patent and Trademark Office*